United States Patent [19]
Roulier et al.

[11] Patent Number: 6,007,830
[45] Date of Patent: Dec. 28, 1999

[54] EXPANDED SOLID COMPOSITION WHOSE MATRIX COMPRISES A STARCH-BASED CELLULAR NETWORK AND WHICH CONTAINS EXPANDED THERMOPLASTIC HOLLOW PARTICLES AND ITS USES IN TOPICAL APPLICATION

[75] Inventors: Véronique Roulier, Paris; Myriam Mellul, L'Hay-Les-Roses; Gérard Gabin, Paris, all of France; Katrin Holz, Lausanne, Switzerland

[73] Assignee: L'Oreal, Paris, France

[21] Appl. No.: 09/252,884

[22] Filed: Feb. 18, 1999

Related U.S. Application Data

[62] Division of application No. 08/654,741, May 29, 1996, Pat. No. 5,925,380.

[30] Foreign Application Priority Data

May 29, 1995 [FR] France ................................. 95-06321

[51] Int. Cl.⁶ ............................... A61K 6/00; A61K 7/00
[52] U.S. Cl. ......................... 424/401; 424/489; 514/844
[58] Field of Search ................... 424/401, 489; 514/844

[56] References Cited

U.S. PATENT DOCUMENTS 3,615,972 10/1971 Morehouse et al. .................... 156/79
5,089,469 2/1992 Zampino et al. ........................ 512/22
5,196,200 3/1993 Wilson et al. .......................... 424/411
5,679,361 10/1997 Pradier et al. ......................... 424/401

FOREIGN PATENT DOCUMENTS

| 0 486 394 | 5/1992 | European Pat. Off. . |
| 0 544 349 | 6/1993 | European Pat. Off. . |
| 0 605 284 | 7/1994 | European Pat. Off. . |
| 1 594 256 | 7/1970 | France . |
| WO 92/08759 | 5/1992 | WIPO . |

*Primary Examiner*—Nathan M. Nutter
*Attorney, Agent, or Firm*—Finnegan, Henderson, Farabow, Garrett & Dunner, L.L.P.

[57] ABSTRACT

The present invention relates to expanded solid compositions whose matrix comprises a cellular network formed from a starch-rich product and contains at least some expanded thermoplastic hollow particles of polymer or copolymer of an ethylenically unsaturated monomer or mixture of such monomers. These compositions constitute new dosage forms for cosmetic or dermatological use. These compositions either take the form of expanded cylinders, pellets, leaves or flakes, or the form of powder. When reduced to the powder state, they may also be used as a make-up or hygiene composition to be rehydrated or to be used as such.

6 Claims, No Drawings

EXPANDED SOLID COMPOSITION WHOSE MATRIX COMPRISES A STARCH-BASED CELLULAR NETWORK AND WHICH CONTAINS EXPANDED THERMOPLASTIC HOLLOW PARTICLES AND ITS USES IN TOPICAL APPLICATION

This is a division of application Ser. No. 08/654,741, filed May 29, 1996 and now U.S. Pat. No. 5,925,380 the contents of which are incorporated herein by reference.

The present invention relates to expanded solid compositions whose matrix comprises a starch-based cellular network and contains expanded thermoplastic hollow particles, as well as to their uses in topical application.

Expanded products based on starch and on edible ingredients, obtained by extrusion in one or more single- or twin-screw extruders, in particular aperitif snacks, crisps, cornflakes, breakfast cereals and biscuits, are known in the food industry.

The inventors have discovered, surprisingly, new dosage forms for cosmetic or dermatological use, in the form of an expanded solid composition whose matrix comprises of a cellular network formed from a starch-rich product and contains expanded thermoplastic hollow particles of homopolymer or copolymer of an ethylenically unsaturated monomer or mixture of such monomers.

The inventors have discovered, moreover, that the compositions of the invention can be obtained by extrusion/expansion, unexpectedly, at temperatures below 100° C., and can thus contain cosmetic or dermatological substances which are heat-sensitive or unstable at temperatures above 100° C.

The compositions according to the invention can constitute new forms of make-up products, such as face powders, eyeshadows or blushers, or new forms of products for hygiene such as dry shampoos or for care such as make-up removal products. They have the appearance of expanded cylinders, pellets, leaves or flakes, and can contain a sufficient amount of fillers to obtain good disintegration and satisfactory softness qualities.

They can, in addition, contain large amounts of a fatty phase, permitting an improvement in comfort and enabling their application to the skin to be facilitated, for example by being able to apply them directly without employing a make-up tool such as a brush, sponge, or powder puff.

The inventors have also discovered, unexpectedly, that the introduction of expanded thermoplastic hollow particles of homopolymer or copolymer of an ethylenically unsaturated monomer or mixture of such monomers into a matrix comprising a starch-based cellular network did not decrease the degree of expansion, and enabled large amounts of fats such as oils and/or waxes to be introduced.

The compositions according to the invention can contain, in particular, in large amounts, waxes imparting properties of film staying power, spreadability and matte effect. The compacted powders customarily used for make-up cannot contain large amounts of fats such as waxes (more than 10% by weight). Their incorporation in powders leads to products which impart a wax coating and which cannot be disintegrated.

The expanded hollow particles of homopolymer or copolymer formed from an ethylenically unsaturated monomer or mixture of such monomers are fillers of very low density, generally less than 0.1 g·cm$^{-3}$ and known for their qualities of softness and of absorption of fats in make-up or care compositions. However, they are also known for the fact that they are difficult to compact.

Filler which is difficult to compact is understood to mean a starting material which, at and above a certain percentage which will depend on the material in question, cannot be compacted by means of a mechanical press. These types of filler cannot be used, in general, in make-up products in the form of compacted powder. Products containing small amounts of this type of filler do not remain fully intact on storage and do not display good impact resistance and/or an acceptable flat surface.

The compositions according to the invention, due to their novel starch-based cellular structure, can hence contain these fillers which are difficult to compact, imparting a very soft and non-greasy feel without having the drawbacks of the make-up compositions of the prior art containing this type of filler.

The compositions of the invention, due to their novel starch-based cellular structure, can constitute new forms of make-up products whose cosmetic qualities are novel, in particular for their softness and their lightness due to the incorporation of fillers of low density.

The compositions according to the invention may take the form of expanded cylinders, pellets, leaves or flakes applied directly to the skin or the face, or be reduced to powder and used as such, in a traditional manner, as make-up powder. They may take the form of powder for care and/or hygiene, applied directly to the skin, scalp or hair, for example dry shampoos or loose powders for body care.

They may also take the form of expanded cylinders, pellets, leaves or flakes, stored in the dry state, and be very readily amenable to rehydration after immersion in an aqueous medium to reconstitute formulations for make-up such as make-up foundations or formulations for care or hygiene such as creams, milks, foam baths, gels and shampoos. It is thus possible to incorporate water-sensitive cosmetic active agents in these dosage forms, which are stable on storage at temperatures below 45° C.

The compositions according to the invention, stored in the dry state and intended to be rehydrated at the time of use to reconstitute cosmetic formulations such as the ones mentioned above, have the advantage, relative to the traditional dosage forms amenable to rehydration, of being very readily amenable to rehydration and, in the context of cleansing compositions, in particular shampoos, of being less damaging as a result of the fact that the surfactants are integrated in a starch-based expanded matrix.

The compositions according to the invention are expanded solid compositions whose matrix comprises a cellular network formed from a starch-rich product and contains at least some thermoplastic hollow particles of homopolymer or copolymer formed from an ethylenically unsaturated monomer or mixture of such monomers.

The particles which can be used according to the invention may be prepared from ethylenically unsaturated monomers which are non-toxic and non-irritating to the skin. The particles of the invention may be obtained, for example, according to the processes of European Patents and Patent Applications EP-056 219, EP-348 372, EP486 080, EP-320 473, EP-112 807 and U.S. Pat. No. 3,615,972, the disclosures of which are hereby incorporated by reference.

The internal cavity of the particles contains, in general, a gas which may be air, nitrogen or a hydrocarbon such as isobutane or isopentane.

Among the monomers used for preparing the expanded thermoplastic hollow particles of the invention, there may be mentioned methacrylic or acrylic acid esters such as methyl acrylate or methacrylate; vinylidene chloride; acrylonitrile; styrene and its derivatives; butadiene and its derivatives; and mixtures thereof.

It is possible, for example, to use methyl acrylate or methacrylate polymers or copolymers, the copolymers formed from styrene and acrylonitrile and the copolymers of vinylidene chloride and acrylonitrile or vinyl chloride.

It is preferable to use a copolymer containing: from 0% to 60% of vinylidene chloride or one of its derivatives, from 20% to 80% of acrylonitrile or one of its derivatives and from 0% to 50% of a (meth)acrylic or styrene monomer, the sum of the percentages (by weight) being equal to 100. The (meth)acrylic monomer is, for example, methyl or ethyl (meth)acrylate. The styrene monomer is, for example, styrene or α-methylstyrene.

More preferably, the particles used in the present invention are hollow particles of an expanded copolymer of vinylidene chloride and acrylonitrile, or of vinylidene chloride, acrylonitrile and methyl methacrylate. These particles may be dry or hydrated.

Advantageously, the particles of the invention have a particle size ranging from 1 µm to 100 µm, preferably ranging from 5 µm to 60 µm, and more preferably from 10 µm to 50 µm.

Preferably, the density of the particles is chosen from within the range extending from 15 kg/m³ to 200 kg/m³, more preferably from 40 kg/m³ to 120 kg/m³, and still more preferably from 60 kg/m³ to 80 kg/m³.

The particles which can be used in the invention are, for example, microspheres of expanded terpolymer of vinylidene chloride, acrylonitrile and methacrylate, sold under the brand name EXPANCEL by the company Casco Nobel and under the references 551 DE 50 (particle size approximately 40 µm), 551 DE 20 (particle size approximately 30 µm and density approximately 65 kg/m³), 551 DE 12 (particle size approximately 12 µm), 551 DE 80 (particle size approximately 80 µm) and 461 DE 50 (particle size approximately 50 µm). It is also possible to use microspheres composed of the same expanded terpolymer having a particle size of approximately 18 µm and a density of approximately 70 kg/m³, referred to below as EL 23.

The expanded thermoplastic hollow particles are present in the compositions of the invention in concentrations preferably ranging from 2 to 30% by weight relative to the total weight of the composition.

The starch-rich products used in the compositions according to the invention are preferably chosen from cereal flours such as wheat flour, corn flour, rice flour, oatmeal and wheat-germ flour or potato flour; pure starches commonly used in foods, such as maize, potato, tapioca and oat starches; starches modified in respect of the amylose/amylopectin ratio, such as the product HYLON VII sold by Amylum; and starches modified by crosslinking or modified with a functional group, such as the crosslinked maize starch sold under the name RESISTAMYL E2 by Amylum, the weakly quaternized maize starch sold under the name MYPLUS W7 by Amylum, the potato starch sold under the name SUPRAMYL P 60 by Amylum or the hydroxypropylated maize starch sold under the name MERIGEL EF6 by Amylum.

The matrix comprising the starch-based cellular network formed from these starch-rich products is present in the compositions according to the invention in a proportion preferably ranging from 70 to 98% by weight relative to the weight of the composition.

The compositions according to the invention possess a water content preferably not exceeding 5% by weight, and more preferably ranging from 1 to 2% by weight, relative to the weight of the composition.

The compositions according to the invention can contain, in addition, a fatty phase. This fatty phase can comprise oils and/or waxes of animal, vegetable, mineral or synthetic origin, alone or mixed.

Among oils which can be used, there may be mentioned mink oil, turtle oil, soya-bean oil, grape-pip oil, sesame oil, maize oil, rape oil, sunflower oil, cottonseed oil, avocado oil, olive oil, castor oil, jojoba oil, groundnut oil; hydrocarbon oils such as liquid paraffin, squalane, petroleum jelly; fatty esters such as isopropyl myristate, isopropyl palmitate, butyl stearate, hexyl laurate, isononyl isononate, 2-ethylhexyl palmitate, 2-hexyldecyl laurate, 2-octyldecyl palmitate, 2-octyldodecyl myristate or lactate, 2-ethylhexyl succinate, diisostearyl malate, glyceryl or diglyceryl triisostearate; silicone oils such as polymethylsiloxanes, polymethylphenylsiloxanes, polysiloxanes modified with fatty acids, fatty alcohols or polyoxyalkylenes, fluorinated silicones, perfluorinated oils; higher fatty acids such as myristic acid, palmitic acid, stearic acid, behenic acid, oleylic acid, linoleic acid, linolenic acid or isostearic acid; and higher fatty alcohols such as cetanol, stearyl alcohol or oleyl alcohol.

Among waxes which can be used, there may be mentioned beeswaxes, lanolin waxes and Chinese insect waxes; carnauba, candelilla and ouricury waxes, cork-fibre waxes, sugar-cane waxes, Japan waxes, hydrogenated jojoba waxes and hydrogenated oils such as hydrogenated sunflower oil, hydrogenated castor oil, hydrogenated coconut oil and hydrogenated lanolin; paraffins, microcrystalline waxes, montan waxes and ozokerites; polyethylene waxes, waxes obtained by Fischer-Tropsch synthesis, waxy copolymers as well as their esters, and silicone waxes such as polyalkoxy- and polyalkylsiloxanes.

The fatty phase is present in proportions preferably ranging from 2 to 30% by weight, and more preferably from 5 to 15% by weight, relative to the total weight of the composition.

The fatty phase can, in addition, comprise additives such as lipophilic cosmetic active agents and/or fat-soluble ingredients generally used in cosmetics, such as perfumes. Preferably, these additives may be present in an amount of 0–20% relative to the total weight of the fatty phase.

The compositions according to the invention can contain, in addition, pigments, preferably in an amount of 0–50% relative to the total weight of the final composition. These pigments may be chosen from inorganic pigments, organic pigments and pearlescent pigments.

Among inorganic pigments, there may be mentioned, for example, titanium dioxide (rutile or anatase), optionally surface-treated; black, yellow, red and brown iron oxides; manganese violet; ultramarine blue; chromium oxide, optionally hydrated; and ferric blue.

Among organic pigments, there may be mentioned, for example, the pigments D & C red, D & C orange, D & C yellow, carbon black and carmine-based lakes.

The pearlescent pigments may be chosen, in particular, from white pearlescent pigments such as titanium oxide-coated mica or bismuth oxychloride; and colored pearlescent pigments such as titanium-mica with iron oxides, titanium-mica with ferric blue or chromium oxide, titanium-mica with an organic pigment of the abovementioned type, as well as bismuth oxychloride-based pigments.

The compositions can also contain other inorganic or organic fillers customarily used in make-up products, such as, for example, talc, micas, kaolin, silica, zinc and titanium oxides, calcium carbonate, magnesium carbonate and magnesium hydrogen carbonate, powders of non-expanded synthetic polymers, and metal soaps derived from $C_8$–$C_{22}$ carboxylic acid. They are present in concentrations preferably ranging from 0 to 50% by weight relative to the weight of the composition.

The compositions according to the invention can also contain one or more nonionic, anionic, cationic or amphoteric surfactant(s) customarily used in cosmetics. The amount of surfactant agent used is preferably from 2 to 30% relative to the total weight of the composition.

The compositions according to the invention can also contain, in addition, water-soluble cosmetic active agents.

Among cosmetic active agents, there may be mentioned antioxidants or free-radical scavengers; hydrating or humectant agents such as glycerol and collagen; and UV screening agents such as benzophenone. These water-soluble active agents may be present in the final composition in an amount of 0 to 20%, and preferably 5 to 15%, by weight. Among heat-sensitive active agents, vitamins such as vitamin E may be mentioned.

Naturally, a person skilled in the art will make sure to choose these possible additional compounds and/or the amounts thereof in such a way that the advantageous properties intrinsically associated with the composition according to the invention are not, or are not substantially, impaired by the addition(s) envisaged.

The present invention also relates to a process for preparing a composition as defined above, characterized in that the latter is preferably obtained from the starch-rich product, thermoplastic hollow particles and possible additional constituents such as are mentioned above in the presence of water, preferably by mixing, kneading and expansion in a twin-screw extruder.

An extruder which can be used for the process of the invention is chosen from twin-screw extruders such as the one described in French Patent Application FR 94/00756, the disclosure of which is hereby specifically incorporated by reference.

The starting materials are introduced at the entry of the twin-screw extruder into the feeding zone at room temperature, preferably at approximately 20° C., are then conveyed to the transport zone, preferably at a temperature of approximately 50° C., and are then kneaded and compressed in various zones of the extruder which are maintained at a temperature below 100° C. and preferably ranging from 60 to 80° C.; the mass obtained is transported to the exit of the extruder and extruded through a die to undergo an expansion thereat; the extruded products are then, if necessary, dried according to a standard drying process, such as an oven or ventilated drying cabinet.

During the mixing phase, the starch-rich product gelatinizes and forms, after extrusion, a cellular network constituting the matrix of the final expanded products.

A surprising advantage of the process of the invention is that the use of thermoplastic hollow particles of polymer or copolymer of ethylenically unsaturated monomer or mixture of such monomers enables an expansion of the compositions to be obtained at temperatures of the order of 60–80° C. This process enables expanded products to be obtained which can contain cosmetic or dermatological substances which are heat-sensitive at temperatures above 100° C., such as vitamins or some oils which degrade above 100° C.

Another subject of the invention consists of new cosmetic or dermatological compositions, characterized in that they comprise an expanded solid composition as defined above. These compositions may take the form of expanded cylinders, pellets, leaves or flakes, or alternatively be reduced to the powder state. These compositions can be make-up products. They may be applied to the face either directly or by means of a make-up tool such as a brush, a powder puff or an applicator pad. They may be stored in the dry state and, at the time of use, rehydrated after immersion in water to reconstitute a liquid or semi-liquid aqueous make-up formulation such as a make-up foundation.

The compositions according to the invention can be products for the care and/or hygiene of the skin, mucosae, scalp or hair. They may take the form of powder and be applied directly to the skin, scalp or hair as for example, a dry shampoo or a loose powder for body care. These compositions may also take the form of powder or alternatively of expanded cylinders, pellets or flakes which are amenable to rehydration after immersion in water so as to reconstitute an aqueous formulation for care and/or hygiene, such as a cream, milk, gel, foam bath or shampoo.

The examples which follow serve to illustrate the invention without, however, limiting its scope.

EXAMPLES

Example 1

Dry Shampoo in the Form of Powder to be Rehydrated

The final product had the following formulation:

| Wheat flour | 35.0% by weight |
|---|---|
| Maize starch | 35.0% by weight |
| Expanded particles of vinylidene chloride/acrylonitrile/methyl methacrylate copolymer sold by Casco Nobel under the name EXPANCEL 550DE | 15.0% by weight |
| Sodium lauryl ether sulphate | 15.0% by weight |

Procedure

The starting materials were introduced at the entry of the extruder at a temperature of 30° C. They were then conveyed to the transport zone, at a temperature of approximately 50° C., and were thereafter kneaded and compressed in various zones of the extruder which were maintained at 60–80° C. The mass thus kneaded and compressed was transported to the exit of the extruder and extruded through a die 5 mm in diameter. The speed of rotation of the screws was 500 rpm. The cylinders obtained at the exit of the die were reduced to the powder state by means of a standard toothed roll crusher placed at the exit of the extruder.

Example 2

Face Mask in the Form of "Expanded Leaves" to be Rehydrated

The final product had the following formulation:

| Wheat flour | 24.0% by weight |
|---|---|
| Starch | 24.0% by weight |
| Expanded particles of vinylidene chloride/acrylonitrile/methyl methacrylate copolymer sold by Casco Nobel the name EXPANCEL 550DE | 10.0% by weight |
| Silica sold by Maprecos under the name SB700 | 40.0% by weight |
| Vitamin E | 2.0% by weight |

Procedure

The starting materials were introduced at the entry of a twin-screw extruder at a temperature of 30° C. They were then conveyed to the transport zone, at a temperature of approximately 50° C., and were thereafter kneaded and compressed in various zones of the extruder which were maintained at 60–80° C. The mass thus kneaded and compressed was transported to the exit of the extruder and extruded through a die 5 mm in diameter. The expanded strips obtained at the exit of the die were cut to the desired size in the form of leaves.

What is claimed is:

1. A process for preparing an expanded and extruded solid composition with a matrix which comprises a cellular network formed from a starch-rich product and which contains expanded thermoplastic hollow particles of a homopolymer or copolymer formed from an ethylenically unsaturated monomer or mixture of such monomers, wherein the starting materials for said process include said starch-rich product, said thermoplastic hollow particles, and water, said process comprising:

mixing said starting materials together to form a mixture in a twin-screw extruder;

kneading said mixture in said extruder; and expanding and extruding said kneaded mixture in said extruder.

2. A process according to claim 1, comprising:

introducing said starting materials at the entry of the twin-screw extruder into the feeding zone at room temperature;

kneading and compressing said materials in various zones of the extruder, said zones being maintained at a temperature below 100° C. to obtain a kneaded and compressed mass;

transporting said mass obtained to the exit of the extruder;

extruding said mass through a die to undergo an expansion and form an extruded product; and if necessary, drying said extruded products according to a standard drying process.

3. A process according to claim 2, further comprising heating the kneading and compression zones to a temperature ranging from 60° to 80° C.

4. A process for preparing an expanded solid composition with a matrix which comprises a cellular network formed from a starch-rich product and which contains expanded thermoplastic hollow particles of a homopolymer or copolymer formed from an ethylenically unsaturated monomer or mixture of such monomers, wherein the starting materials for said process include said starch-rich product, said thermoplastic hollow particles, and water, said process comprising:

mixing said starting materials together to form a mixture and processing said mixture to obtain said expanded solid composition.

5. A process as claimed in claim 1, wherein said particles are present in a proportion of 2 to 30% relative to the total weight of said composition.

6. A process as claimed in claim 4, wherein said particles are present in a proportion of 2 to 30% relative to the total weight of said composition.

* * * * *